United States Patent
Scher et al.

(10) Patent No.: US 6,340,653 B1
(45) Date of Patent: Jan. 22, 2002

(54) MICROENCAPSULATED ACETOCHLOR HERBICIDAL COMPOSITION

(75) Inventors: Herbert B. Scher, Moraga; Marius Rodson, El Sobrante, both of CA (US)

(73) Assignee: Syngenta Limited, Surrey (GB)

( * ) Notice: Subject to any disclaimer, the term of this patent is extended or adjusted under 35 U.S.C. 154(b) by 0 days.

(21) Appl. No.: 08/453,611

(22) Filed: May 30, 1995

Related U.S. Application Data

(63) Continuation of application No. 08/065,282, filed on May 20, 1993, now abandoned, which is a continuation of application No. 07/651,900, filed on Feb. 6, 1991, now abandoned.

(51) Int. Cl.[7] .......................... A01N 25/28; A01N 37/22
(52) U.S. Cl. ...................... 504/112; 504/342; 504/359
(58) Field of Search ............................... 504/112, 342, 504/359; 71/DIG. 1

(56) References Cited

U.S. PATENT DOCUMENTS

| 4,140,516 A | * | 2/1979 | Scher | 71/88 |
| 4,285,720 A | * | 8/1981 | Scher | 71/88 |
| 4,417,916 A | * | 11/1983 | Beestman et al. | 71/DIG. 1 |
| 4,640,709 A | * | 2/1987 | Beestman | 71/100 |
| 4,938,797 A | * | 7/1990 | Hässlin et al. | 71/118 |
| 5,006,161 A | * | 4/1991 | Hässlin et al. | 71/118 |

FOREIGN PATENT DOCUMENTS

EP 0252896 * 1/1988

\* cited by examiner

*Primary Examiner*—S. Mark Clardy
(74) *Attorney, Agent, or Firm*—Hale and Dorr LLP

(57) ABSTRACT

Microencapsulated compositions containing haloacetanilide herbicides, i.e., acetochlor, are produced by microencapsulation process. The microencapsulated composition performs comparably to nonencapsulated compositions of the same herbicide applied at the same application rates.

31 Claims, No Drawings

MICROENCAPSULATED ACETOCHLOR HERBICIDAL COMPOSITION

RELATED APPLICATIONS

This application is a continuation of application No. 08/065,282 filed May 20, 1993, now abandoned, which is a continuation of application No. 07/651,900 filed Feb. 6, 1991, now abandoned.

FIELD OF THE INVENTION

This invention relates to microencapsulated herbicidal compositions containing a haloacetanilide herbicide, and processes for preparation and for use of such compositions.

BACKGROUND AND PRIOR ART

The haloacetanilides, particularly the subclass generally known as α-chloroacetanilides, are a well-known class of herbicidal agents and have been used and proposed for use in a number of crop and non-crop applications. Some of the better known members of this class include α-chloro-6'-ethyl-N-(2-methoxy-1-methylethyl)-acetanilide (metolachlor), N-butoxymethyl-α-chloro-2',6'-diethylacetanilide (butachlor), α-chloro-2',6'-diethyl-N-methoxymethylacetanilide (alachlor), 2-chloro-N-(ethoxymethyl)-6'-ethyl-o-acetotoluidide (acetochlor) and α-chloro-N-isopropylacetanildie (propachlor). Many other compounds of this type are disclosed in numerous patents.

Various patents and publications describe the production and application of microencapsulated formulations of haloacetanilide herbicides. These include U.S. Pat. Nos. 4,280,833; 4,417,916; 4,534,783; 4,563,212; and 4,640,709. Additionally, U.S. Pat. No. 4,936,901 discloses herbicidal compositions which are dry flowable water-dispersible granular formations comprising a mixture of microcapsules of a water-insoluble pesticide (including a haloacetanilide herbicide) encapsulated within a polymeric shell wall and at least one other pesticide which is nonencapsulated.

In the patents just mentioned, the microcapsule is formed in general with a shell wall of polyurea which is prepared in general from an aqueous phase material containing, for example, an emulsifier, and a water-immiscible phase consisting essentially of polymethylene polyphenylisocyanate and a water-immiscible herbicide, such as a haloacetanilide herbicide. To that is added, with agitation, a polyfunctional amine, which reacts with the polyphenylisocyanate to form a polyurea shell wall around the water-immiscible phase. This basic process is described in U.S. Pat. No 4,280,833. The remaining patents and patent application describe improvements in the process or microcapsules formed, such as specific emulsifiers which may be used in preparation of these microcapsules.

Microcapsule formulations are employed to achieve a slow or controlled release of the material encapsulated (in the present case, a water-immiscible haloacetanilide herbicide) into the surrounding or external medium. When properly done, the results are greater longevity of the encapsulated material and longer availability of it for its intended purpose. In the case of herbicides, microencapsulation provides a means for obtaining longer effective life of the herbicide in the surrounding medium, for instance in the soil, through a controlled released.

This benefit of increased longevity, however, can be offset by lack of sufficient activity of the material in the early period after application, and/or at relatively low application rates. Presumably this occurs because shortly after application, or at low rates, or both, there has been insufficient release of the active material (e.g. herbicide) to provide effective results, particularly in comparison with similar material applied in nonencapsulated form.

A typical comparison of the behavior of encapsulated as opposed to nonencapsulated forms of haloacetanilide herbicides is found in Example 17 of U.S. Pat. No. 4,280,833 (the same information is in Example 30 of U.S. Pat. No. 4,417, 916). This example compares the performance of encapsulated and nonencapsulated (emulsifiable concentrate) forms of the haloacetanilide herbicide alachlor at varying concentrations and over a period of time. In the procedure of this example, alachlor is applied to weeds planted in aluminum pans at application rates ranging from 1.0 lb./acre down to 0.0078 lb./acre. As the example states, the results indicate that microencapsulated alachlor exhibited longer soil longevity than unencapsulated alachlor applied at the same rates. However, the same example also indicates that at the first rating period, two weeks after planting, the activity of encapsulated alachlor began to decrease at application rates below 0.5 lbs./acre on barnyardgrass and below 0.25 lbs./acre on crabgrass and green foxtail. Indeed, at an application rate of 0.0625 lbs./acre, the encapsulated alachlor was rated "0" on barnyardgrass and green foxtail, whereas the unencapsulated alachlor received ratings of 100 and 70, respectively.

Another process for production of microencapsulated forms of pesticides, including herbicides, is disclosed in U.S. Pat. No. 4,285,720. This process involves the preparation of microcapsules by a technique generally known as in situ interfacial condensation polymerization. In general, in the process described in U.S. Pat. No. 4,285,720, microencapsulated formulations containing pesticides are prepared by the steps of (a) providing, at room temperature, a dispersion of (i) a water-immiscible phase comprising a water-immiscible material (e.g., pesticide) to be encapsulated and an organic polyisocyanate in (ii) an aqueous phase comprising a solution of water, a surfactant and a protective colloid; and a (b) heating and maintaining said dispersion in a temperature range from about 40° C. to about 90° C.; where part of the water-immiscible material is encapsulated within discrete polyurea capsular enclosures.

U.S. Pat. No. 4,285,720 deals with the encapsulation of water-immiscible substances in general and contains examples showing encapsulation of water-immiscible organophosphorus insecticides, thiocarbamate herbicides, an insect hormone mimic, and an organophosphorus flame retardant. Another example shows the encapsulation of two water-immiscible substances by this process. Various products which can be encapsulated are discussed generally and specifically in columns 13 and 14. This patent does not, however, mention haloacetanilide herbicides as one type of substance which may be encapsulated by the process described.

Two other patents which describe modifications or improvements to the process described in U.S. Pat. No. 4,285,720 do include mention of haloacetanilide herbicides. U.S. Pat. No. 4,140,516 describes the use of a phase transfer catalyst in a process such as that described in U.S. Pat. No. 4,285,720, and mentions several haloacetanilide herbicides in column 12 to which the process may be applied. U.S. Pat. No. 4,448,929 describes an improved protective colloid for use in the process of U.S. Pat. No. 4,285,720 (among others) and mentions metolachlor and butachlor as two materials to which that modification may be applied.

SUMMARY OF THE INVENTION

It has now been found that use of the process as described in U.S. Pat. No. 4,285,720 can produce microencapsulated compositions of haloacetanilide herbicides which have the dual benefits of providing comparable herbicidal activity to nonencapsulated formulations of the same herbicide, even in the early stages of application and/or at lower application rates, while maintaining substantially lower mammalian toxicity compared with the nonencapsulated formulations.

DETAILED DESCRIPTION OF THE INVENTION

In accordance with the invention, a microencapsulated formulation of a haloacetanilide herbicide is produced in accordance with the process described and disclosed in U.S. Pat. No. 4,285,720. The contents of said U.S. patent are hereby incorporated by reference herein.

In brief, the process involves the encapsulation of a water-immiscible material, in this case a water-immiscible α-haloacetanilide (preferably α-chloroacetanilide) herbicide within discrete capsules of polyurea without addition of a second reactant. Most preferably, the herbicide is a 2-chloro-N-(ethoxymethyl)-6'-ethyl-o-acetotoluidide (acetochlor). In the process, hydrolysis of an isocyanate monomer to form an amine takes place, and that in turn reacts with another isocyanate monomer to form polyurea. In general, two steps comprise the process.

In the first step, a physical dispersion of a water-immiscible phase in an aqueous phase is prepared. The water-immiscible phase comprises the haloacetanilide herbicide to be encapsulated together with other material as described below. As opposed to the process described in U.S. Pat. No. 4,150,516, a phase transfer catalyst is not utilized (as a component of the water-immiscible or organic phase). The aqueous phase is comprised of water, a suitable surfactant, and a material termed a "protective colloid".

In the second step, the dispersion is maintained in a temperature range of from about 20° C. to about 90° C. during which the condensation reaction takes place to form the polyurea, at the interfaces between the droplets of the organic phase and the aqueous phase. Adjustment of the pH of the resulting mixture and the temperature within the desired temperature range during the second step advances to condensation reaction.

The aqueous phase is prepared from water, a surfactant, and a protective colloid. In general, the surfactant or surfactants in this phase may be anionic, cationic or non-ionic surfactants with an HLB range of from about 12 to about 16. Suitable surfactants include polyethylene glycol ethers of linear alcohols, ethoxylated nonylphenols, naphthalene sulfonates, and the like. Particularly preferred surfactants include block copolymers of propylene oxide and ethylene oxide and anionic/nonionic blends.

The protective colloid present in the aqueous (or continuous) phase can be selected from a wide range of such materials including polyalkylates, methyl cellulose, polyvinyl alcohol, polyacrylamide, poly(methylvinyl ether/maleic anhydride), graft copolymers of polyvinyl alcohol and methylvinyl ether/maleic acid (hydrolyzed methylvinyl ether/maleic anhydride; see U.S. Pat. No. 4,448,929, which is hereby incorporated by reference herein), and alkali metal or alkaline earth metal lignosulfonates. Preferably, however, the protective colloid is selected from alkali metal and alkaline earth metal lignosulfonates, most preferably sodium lignosulfonates.

In general, the range of surfactant concentration in the process is from about 0.01 to about 3.0 percent by weight, based on the aqueous phase, but higher concentrations of surfactant may also be used. The protective colloid is generally present in the aqueous phase in an amount of from about 0.1 to about 5.0 percent by weight. The amount of protective colloid employed will depend on various factors, such as molecular weight, compatibility, etc. The protective colloid can be added to the aqueous phase prior to the addition of the organic phase, or can be added to the overall system after the addition of the organic phase or the dispersion of it.

The organic phase comprises the haloacetanilide herbicide to be encapsulated and one or more polyisocyanates. A water-immiscible organic solvent may also be used to dissolve both the haloacetanilide herbicide and the polyisocyanate. Preferably the organic phase, and at least the haloacetanilide and polyisocyanate are premixed to obtain a homogeneous phase before addition to the aqueous phase.

Depending on the nature of the haloacetanilide herbicide and the intended application or use of this microencapsulated product, the compositions of this invention may also include a herbicide safener or antidote. Many such safeners or antidotes are well known in the art. Preferred types for use with haloacetanilide herbicides include dichloroacetamides such as dichlormid (N,N-diallyl dichloroacetamide); 2,2,5-trimethyl-3-dichloroacetyl oxazolidine (R-29148), N-dichloroacetyl-1-oxa-4-azaspiro[4,5]decane (AD-67); 4-dichloroacetyl-2,3-dihydro-3-methyl-1,4-benzoxazine (CGA-154281); 1-(dichloroacetyl)hexahydro-3,3,8a-trimethylpyrrolo-[1,2-a]-pyrimidin-6(2H)-one and N-(1,3-dioxolan-2-yl-methyl)-N-(2-propenyl)-2,2-dichloroacetamide (PPG-1292).

These and other dichloroacetamides are described, for instance, in U.S. Pat. Nos. 4,124,372; 4,256,481; 4,294,764; 4,448,960; 4,601,745; 4,618,361; 4,708,735 and 4,900,350. Additional known types of safeners or antidotes include certain oxime derivatives (U.S. Pat. Nos. 4,070,389 and 4,269,755, for instance), thiazole carboxylic acids and derivatives (U.S. Pat. No. 4,199,506 for instance), haloacyltetrahydroisoquinolines (U.S. Pat. No. 4,755,218, for example), aryl cyclopropane carbonitriles (U.S. Pat. No. 4,859,232, for example) and 1,8-naphthalic acid, its anhydride and derivatives.

Safeners or antidotes, when included, will usually be contained in the organic or water-immiscible phase.

The polyisocyanates which may be used in this invention are those described in U.S. Pat. No. 4,285,720. A single compound or a mixture of two or more polyisocyanates may be used. Mixtures are preferred. Of the polyisocyanates, polymethylene polyphenylisocyanate (PAPI), and isomeric mixtures of tolylene diisocyanate (TDI) are preferred. Particularly preferred are mixtures of polymethylene polyphenylisocyanate with isomeric mixtures of tolylene diisocyanate, in a weight ratio of PAPI:TDI of from about 1:4 to about 4:1.

The amount of the organic polyisocyanate used in the process will determine the wall content of the microcapsules formed. In general, the polyisocyanate (or microcapsule wall formed from it) will comprise from about 2.0 to about 75.0 percent by weight of the microcapsule. Most preferably the wall will comprise from about 4 to about 15% by weight, of the microcapsule.

The haloacetanilide herbicide itself may be used as a solvent for the polyisocyanates. Alternatively, additional solvents such as xylene may be used (see Canadian Patent 1,094,402).

To obtain the appropriate dispersion, the organic phase, preferably in a premixed homogeneous state, is added to the aqueous phase, with stirring. A suitable dispersing means is employed to disperse the organic phase in the liquid phase. The means may be any high shear device, so as to obtain a desired droplet (and corresponding microcapsule particle) size within the range of from about 0.5 to about 4,000 microns. Preferably the droplet size is from about 1 to about 100 microns, most preferably from about 5 to about 20 microns, average. Once the proper droplet size is obtained, the dispersion means is discontinued. Only mild agitation is required for the remainder of the process.

To form the microcapsules, the temperature of the two-phase mixture is raised to a value of from about 20° C. to about 90° C., preferably from about 40° C. to about 90° C., most preferably from about 40° C. to about 60° C. Depending on the system, as described in U.S. Pat. No. 4,285,720, the pH value may be adjusted to an appropriate level.

The following are examples of preparations of compositions of this invention.

General Procedure

In the examples which follow, the compositions were prepared by the following general procedure:

The organic phase was added to the aqueous phase, and an oil-in-water emulsion was formed by means of a high shear stirrer. The average particle size was in the range of 11.0± 2 microns. While mild agitation was maintained, the temperature of the batch was raised to 50° C. over a period of 30 minutes, and held at 50° C. for 3 hours. The resulting microcapsule suspension was then allowed to cool to room temperature. The additional ingredients were than added and the pH was then adjusted to 11.0 with 50% caustic.

EXAMPLE I

[10911-43; RF-17431]

A composition was prepared using the general procedure described above with the following ingredients.

| Component | Weight, g. | Weight % |
|---|---|---|
| AQUEOUS PHASE | | |
| protective colloid: Daxad 23 (sodium lignosulfonate) | 11.6 | 1.43 |
| surfactant: Pluronic L-64 (20% solution in water) | 9.6 | 1.18 |
| water | 365.0 | 44.83 |
| ORGANIC PHASE | | |
| acetochlor (technical grade- 97.4% purity) | 326.3 | 40.09 |
| N,N-diallyldichloroacetamide (technical grade-96.0% purity) | 55.2 | 6.78 |
| polymethylene polyphenylisocyanate | 20.6 | 2.53 |
| tolylene diisocyanate (mixture of 80% 2,4- and 20% 2,6- isomers) | 10.5 | 1.29 |
| ADDITIONAL INGREDIENTS suspending agents: | | |
| attapulgite (Attagel 40) | 8.0 | 0.98 |
| xanthan gum (Kelzan) | 0.56 | 0.07 |
| buffering agent (sodium carbonate) | 5.7 | 0.70 |
| biocide (Proxel GXL) | 0.8 | 0.10 |
| flocculant (27.5% aluminum silicate) | 0.2 | 0.02 |
| TOTAL | 814.06 | 100.00 |

The resulting microencapsulated product had an average particle diameter (after final treatment) of 11.2 microns.

EXAMPLE II

[11666-14]

Following the procedures and using the ingredients of Example 1, in similar proportions, a five-fold larger batch of product was prepared. The resulting microencapsulated product had an average particle diameter (after final treatment) of 10.2 microns.

EXAMPLE III

[11666-40]

Using the general procedures described above, a composition was prepared from the following ingredients.

| Component | Weight, g. | Weight % |
|---|---|---|
| AQUEOUS PHASE | | |
| protective colloid: Daxad 23 | 5.4 | 1.33 |
| surfactants (anionic/nonionic blends): | | |
| Atlox 3409F | 1.1 | 0.27 |
| Atlox 3404F | 0.2 | 0.05 |
| water | 173.5 | 42.64 |
| ORGANIC PHASE | | |
| acetochlor (technical grade- 95% purity) | 98.6 | 24.24 |
| acetochlor (technical grade, 91.3% purity) | 76.0 | 18.68 |
| N,N-diallyldichloroacetamide (technical grade, 95% purity) | 27.6 | 6.78 |
| polymethylene polyphenylisocyanate (PAPI 135) | 10.9 | 2.68 |
| tolylene diisocyanate (mixture of 80% 2,4- and 20% 2,6- isomers) | 5.5 | 1.35 |
| ADDITIONAL INGREDIENTS | | |
| thickener-attapulgite (Attagel 40) | 4.0 | 0.98 |
| thickener-xanthan gum (Kelzan) | 0.28 | 0.07 |
| buffer (sodium carbonate) | 2.9 | 0.71 |
| biocide (Proxel GXL) | 0.4 | 0.10 |
| flocculant (aluminum silicate) | 0.5 | 0.12 |
| TOTAL | 406.78 | 100.00 |

The resulting encapsulated product had an average particle size (after final treatment) of 11.5 microns.

HERBICIDAL EVALUATIONS

The compositions prepared in the above examples were submitted for herbicidal evaluation in comparison with an emulsifiable concentrate containing the same herbicide and antidote. The emulsifiable concentrate contained 77.94 weight percent acetochlor herbicide (expressed as active ingredient), 12,97% N,N-diallyldichloroacetamide antidote, an emulsifier and Aromatic 100 xylene range solvent (Exxon Chemical Co., Houston, Tex.).

A test procedure was as follows.

Pre-emergence Surface Treatment

Seeds of the indicated plant varieties were planted in flats and watered. Sprayable solutions were prepared by diluting the microencapsulated formulations and the emulsifiable concentrate with water. About one week after planting, the flats were sprayed with the solutions at application rates ranging from 0.06 lbs./acre (0.07 kg/ha) to 2.0 lbs./acre (2.24 kg/ha). Subsequent to the spraying, the plants were evaluated for injury at the times indicted below. Injury was visually evaluated using a scale ranging from 0 to 100, with 0 representing no injury as compared to an untreated controlled flat, and 100 representing complete kill.

The results of these tests are given below in Tables I and II with the injury ratings representing an average of three replications for each test. Plants utilized in the tests are represented by the following abbreviations in these tables.

CN - corn variety T-11
SOY - soybeans, Corsoy variety
ML - milo variety R10
ROM - milo, rox orange
SV - green foxtail, *Setaria viridis*
SF - giant foxtail, *Setaria faberi*
WPM - white proso millet, *Panicum miliaceum*
SH - shattercane, *Sorghum bicolor*

TABLE 1 rated: 19 days after treatment

| Test Composition | rate, lb./acre | % Injury | | | | | |
|---|---|---|---|---|---|---|---|
| | | CN | SOY | ML | SH | SV | WPM | AVG* |
| emulsifiable concentrate | 0.06 | 0 | 18 | 40 | 77 | 98 | 63 | 79 |
| | 0.125 | 0 | 23 | 83 | 95 | 100 | 87 | 94 |
| | 0.25 | 15 | 38 | 95 | 98 | 100 | 95 | 98 |
| | 1.0 | 15 | 60 | 100 | 100 | 100 | 98 | 99 |
| | 2.0 | 17 | 78 | 100 | 100 | 100 | 100 | 100 |
| microencapsulated (Ex. I) | 0.06 | 0 | 25 | 47 | 70 | 100 | 85 | 85 |
| | 0.125 | 0 | 25 | 93 | 97 | 100 | 87 | 95 |
| | 0.25 | 0 | 30 | 95 | 98 | 100 | 95 | 98 |
| | 1.0 | 0 | 62 | 100 | 100 | 100 | 98 | 99 |
| | 2.0 | 7 | 70 | 100 | 100 | 100 | 100 | 100 |

*average injury to three weed species: SH, SV, WPM

TABLE 2 rated: 32 days after treatment

| Test Composition | rate, lb./acre | % Injury | | | | | |
|---|---|---|---|---|---|---|---|
| | | CN | SOY | ML | ROM | SF | WPM | AVG* |
| emulsifiable concentrate | 0.06 | 0 | 0 | 5 | 37 | 100 | 98 | 78 |
| | 0.125 | 0 | 12 | 75 | 91 | 100 | 95 | 95 |
| | 0.25 | 0 | 27 | 96 | 93 | 100 | 100 | 98 |
| | 0.5 | 0 | 43 | 98 | 100 | 100 | 100 | 100 |
| | 1.0 | 0 | 70 | 100 | 100 | 100 | 100 | 100 |
| | 2.0 | 0 | 72 | 100 | 100 | 100 | 100 | 100 |
| microencapsulated (Ex. II) | 0.06 | 0 | 0 | 15 | 37 | 100 | 98 | 78 |
| | 0.125 | 0 | 8 | 85 | 93 | 100 | 99 | 95 |
| | 0.25 | 0 | 23 | 88 | 93 | 100 | 100 | 98 |
| | 0.5 | 0 | 45 | 100 | 100 | 100 | 98 | 99 |
| | 1.0 | 0 | 63 | 100 | 100 | 100 | 100 | 100 |
| | 2.0 | 0 | 53 | 100 | 100 | 100 | 100 | 100 |
| microencapsulated (Ex. III) | 0.06 | 0 | 0 | 18 | 53 | 100 | 93 | 82 |
| | 0.125 | 0 | 7 | 93 | 93 | 100 | 98 | 97 |
| | 0.25 | 0 | 22 | 99 | 100 | 100 | 100 | 100 |
| | 0.5 | 0 | 45 | 98 | 100 | 100 | 100 | 100 |
| | 1.0 | 0 | 57 | 100 | 100 | 100 | 100 | 100 |
| | 2.0 | 0 | 70 | 100 | 100 | 100 | 100 | 100 |

*average injury to three weed species: ROM, SF, WPM

As can be seen from the above tables, the microencapsulated compositions prepared according to this invention performed comparably in all respects to the emulsifiable concentrate, at the same application rates.

Toxicological evaluation of a composition of this invention showed that it exhibited substantially lower mammalian toxicity as compared to emulsifiable concentrates containing acetochlor, particularly in oral toxicity tests. This combination of comparable herbicidal activity (even at low rates or early applications) and lower toxicity, compared with non-encapsulated compositions, is unexpected. It would normally have been expected that a substantial decrease in toxicity would be accomplished by a decrease in herbicidal effectiveness.

What is claimed is:

1. Capsules capable of controlled release of encapsulated organic material comprising 2-chloro-N-(ethoxymethyl)-6'-ethyl-o-acetololuidide herbicide enclosed in a polyurea capsule produced by the process comprising encapsulating water-immiscible material within discrete capsules of polyurea without addition of a second reactant, whereby hydrolysis of an isocyanate monomer to form an amine takes place which in turn reacts with another isocyanate monomer to form polyurea, which comprises the steps of: a) providing, at room temperature, a dispersion of (i) a water-immiscible phase comprising the herbicide and an organic polyisocyanate in (ii) an aqueous phase comprising a solution of water, a surfactant and a protective colloid; and b) heating and maintaining said dispersion in a temperature range from about 40° C. to about 90° C., whereupon said herbicide is encapsulated within discrete polyurea capsular enclosures.

2. Capsules according to claim 1 in which the water-immiscible phase further comprises an herbicide safener or antidote suitable for use with the herbicide.

3. Capsules according to claim 2 in which the safener or antidote is a dichloroacetamide.

4. Capsules according to claim 1 in which the protective colloid is an alkali metal or alkaline earth metal lignosulfonate.

5. Capsules according to claim 4 in which the protective colloid is sodium lignosulfonate.

6. Capsules according to claim 1 in which the organic polyisocyanates is polymethylene polyphenylisocyanate.

7. Capsules according to claim 1 wherein the polyisocyanate is an isomeric mixture of tolylene diisocyanate.

8. Capsules according to claim 1 in which the polyisocyanate is a mixture of polymethylene polyphenylisocyanate and an isomeric mixture of tolylene diisocyanate.

9. Capsules according to claim 8 in which the weight ratio of polymethylene polyphenylisocyanate to tolylene diisocyanate is from about 1:4 to about 4:1.

10. Capsules according to claim 1 in which the dispersed water-immiscible phase comprises droplets having an average particle size of from about 1 to about 100 microns.

11. Capsules according to claim 8 in which the dispersed water-immiscible phase comprises droplets having an average particle size of from about 1 to about 100 microns.

12. Capsules according to claim 9 in which the dispersed water-immiscible phase comprises droplets having an average particle size of from about 1 to about 100 microns.

13. Capsules according to claim 10 in which the dispersed water-immiscible phase comprises droplets having an average particle size of from about 5 to about 20 microns.

14. Capsules according to claim 8 in which the dispersed water-immiscible phase comprises droplets having an average particle size of from about 5 to about 20 microns.

15. Capsules according to claim 9 in which the dispersed water-immiscible phase comprises droplets having an average particle size of from about 5 to about 20 microns.

16. Capsules according to claim 1 in which the organic polyisocyanate comprises from about 4 to about 15% by weight of the capsule.

17. Capsules according to claim 10 in which the organic polyisocyanate comprises from about 4 to about 15% by weight of the capsule.

18. Capsules according to claim 11 in which the organic polyisocyanate comprises from about 4 to about 15% by weight of the capsule.

19. Capsules according to claim 12 in which the organic polyisocyanate comprises from about 4 to about 15% by weight of the capsule.

20. Capsules according to claim 13 in which the organic polyisocyanate comprises from about 4 to about 15% by weight of the capsule.

21. Capsules according to claim 14 in which the organic polyisocyanate comprises from about 4 to about 15% by weight of the capsule.

22. Capsules according to claim 15 in which the organic polyisocyanate comprises from about 4 to about 15% by weight of the capsule.

23. Capsules according to claim 1 containing from about 5 to about 50 weight percent herbicide, and from about 0 to about 10 weight percent of a haloacetanilide herbicide safener or antidote, and prepared using from about 0.1 to about 2.0 weight percent surfactant and about 0.5 to about 5.0 weight percent protective colloid.

24. Capsules according to claim 1 containing from about 25 to about 40 weight percent herbicide, and from about 0 to about 10 weight percent of a haloacetanilide herbicide safener or antidote, and prepared using from about 0.1 to about 1.0 weight percent surfactant and about 0.5 to about 3.0 weight percent protective colloid.

25. Capsules according to claim 1 in which the encapsulated organic material consists essentially of 2-chloro-N-(ethoxymethyl)-6'-ethyl-o-acetotoluidide herbicide and optionally a safener or antidote suitable for use with the herbicide.

26. Capsules according to claim 25 in which the encapsulated material includes a safener or antidote.

27. Capsules according to claim 26 in which the safener or antidote is a dichloroacetamide.

28. Capsules according to claim 25 in which the organic polyisocyanate is polymethylene polyphenylisocyanate.

29. Capsules according to claim 25 in which the organic polyisocyanate is an isomeric mixture of tolylene diisocyanate.

30. Capsules according to claim 25 in which the organic polyisocyanate is a mixture of polymethylene polyphenylisocyanate and an isomeric mixture of tolylene diisocyanate.

31. Capsules according to claim 30 in which the weight ratio of polymethylene polyphenylisocyanate to tolylene diisocyanate is from about 1:4 to about 4:1.

\* \* \* \* \*